United States Patent [19]
Tawarayama et al.

[11] Patent Number: 5,783,740
[45] Date of Patent: Jul. 21, 1998

[54] ANALYTICAL SYSTEM FOR TRACE ELEMENT

[75] Inventors: Naomi Tawarayama, Yokohama; Tadafumi Kuroishi, Naka-gun, both of Japan

[73] Assignee: Hitachi, Ltd., Tokyo, Japan

[21] Appl. No.: 794,699

[22] Filed: Feb. 4, 1997

[30] Foreign Application Priority Data

Feb. 9, 1996 [JP] Japan ................................. 8-023769

[51] Int. Cl.$^6$ .................... G01N 30/02; G01N 27/04; G01N 33/00; B01D 15/08
[52] U.S. Cl. .................. 73/19.1; 73/19.1; 73/23.34; 73/61.43; 73/31.02; 73/61.71; 422/68.1; 422/93
[58] Field of Search .................... 73/19.1, 23.34, 73/23.3, 24.41, 24.42, 61.41, 61.43, 61.56, 61.71, 31.02, 31.03; 422/93, 68.1, 70

[56] References Cited

U.S. PATENT DOCUMENTS

| | | | |
|---|---|---|---|
| 3,703,355 | 11/1972 | Takahashi et al. | 23/230 PC |
| 4,467,038 | 8/1984 | Scott | 436/115 |
| 4,663,724 | 5/1987 | Onizuka et al. | 364/496 |
| 4,708,013 | 11/1987 | Landis | 73/23.1 |
| 4,838,098 | 6/1989 | Barney | 73/19 |
| 4,838,706 | 6/1989 | Coey et al. | 374/54 |
| 5,048,322 | 9/1991 | Hiller et al. | 73/23.41 |
| 5,076,909 | 12/1991 | Overfield et al. | 208/177 |
| 5,106,756 | 4/1992 | Zaromb | 436/161 |
| 5,127,258 | 7/1992 | Brown et al. | 73/191 |
| 5,248,616 | 9/1993 | Beckman et al. | 436/116 |
| 5,454,258 | 10/1995 | Capuano | 73/61.43 |
| 5,521,510 | 5/1996 | Schunck et al. | 324/439 |
| 5,547,497 | 8/1996 | Klemp et al. | 96/104 |
| 5,565,172 | 10/1996 | Capuano et al. | 422/83 |
| 5,637,787 | 6/1997 | Fukushima et al. | 73/23.35 |

FOREIGN PATENT DOCUMENTS 1229963  9/1989  Japan ................................. 73/23.35

Primary Examiner—Hezron E. Williams
Assistant Examiner—J. David Wiggins
Attorney, Agent, or Firm—Kenyon & Kenyon

[57] ABSTRACT

An analytical system for a trace element, which includes a pressure pump for continuously feeding a carrier solution, a first sample introduction unit for introducing a sample and a reagent using sample loops and switching valves, a first flow passage including a pre-treatment unit for pre-treating the sample by heating, and a second flow passage separated from in pressure from the first flow passage, wherein the sample pre-treated in the first flow passage is sampled into the second flow passage through a second sample introduction unit, and the sample thus sampled in the second flow passage is allowed to coloredly react with a coloring agent and measured in absorbance.

15 Claims, 3 Drawing Sheets

FIG.3
| | PRESENT INVENTION 750 | FLOW INJECTION ANALYSIS 760 |
|---|---|---|
| SAMPLE STATE IN FLOW CELL | FLOW CELL / COLORED SUBSTANCE | COLORED SUBSTANCE / FLOW CELL / → FLOW |
| DETECTION PATTERN | ΔAbs ↕ → TIME | ΔAbs ↕ → TIME |
FIG.4
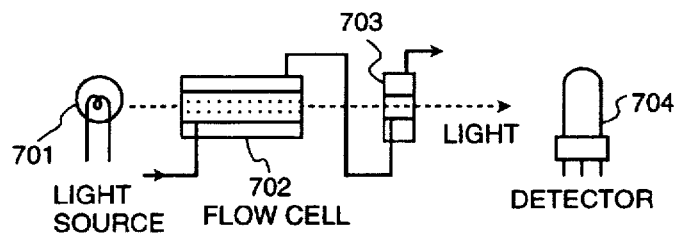
701 LIGHT SOURCE — 702 FLOW CELL — 703 — LIGHT — 704 DETECTOR
FIG.5
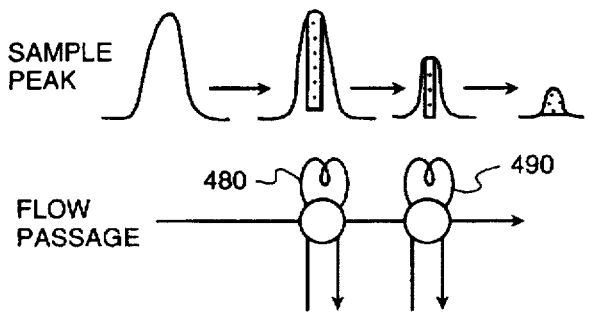
SAMPLE PEAK
FLOW PASSAGE — 480 — 490

5,783,740

ANALYTICAL SYSTEM FOR TRACE ELEMENT

BACKGROUND OF THE INVENTION

The present invention relates to an analytical system for a trace element, and particularly to an analytical system for a trace element which is suitable for quantitative analysis of a total phosphorus and/or a total nitrogen in water using a FIA (Flow Injection Analysis).

For example, a typical quantitative analysis for orthophosphoric acid has been described in a reference [J. Ruzika, E. H. Hansen: "Flow Injection Analysis", p. 178 (1983)], in which ions of orthophosphoric acid reacts with ions of molybdic acid in an acidic solution to produce molybdophosphoric acid, followed by reduction with ascorbic acid, and the resultant colored (in blue) substance is measured in terms of optical absorbance.

It is also known from references [Hirai et al.: Anal. Chem. Acta., 115, 269–277 (1980) and Japanese Patent Publication No. Hei 6–97207] that a total phosphoric salt can be quantitatively analyzed by performing a decomposing operation through heating of a flow passage in a FIA (Flow Injection Analysis).

In the above analysis, a series of operations of sample injection, heating/decomposition, coloring reaction, and detection of absorbance are continuously performed in a specified pressurized flow. Such an analysis presents a problem on the basis of the fact that a time required for heating/decomposition is dependent on a length of the heated flow passage. Namely, if the flow passage has a sufficient length to perfectly decompose a sample by heating, it takes a lot of time for measurement and analytical sensitivity is degraded because of dispersion of the sample. On the contrary, if the heated flow passage has a short length, heating/decomposition becomes imperfect, with a result that the recovery is dependent on the composition of the sample.

Another problem of this analysis is due to the fact that the sample is detected in a state in which a substance colored by reaction of the sample with a coloring reagent continuously flows in a flow cell of the detector. In such a state, the sample in the flow cell forms a laminar flow, and consequently, distribution of the substance becomes non-uniform, with a result that there is a difficulty in detection of a sample, particularly, a low concentration sample.

SUMMARY OF THE INVENTION

An object of the present invention is to provide an analytical system for a trace element, in which a pressurized portion of a flow passage is shortened so as to reduce a time required for measurement and hence to reduce dispersion of a sample, resulting in the reduced total cost of the system.

Another object of the present invention is to provide an analysis system for a trace element, which is aimed at high accurate analysis of a low concentration sample in a still and non-laminar flow state.

To achieve the above objects, according to the present invention, there is provided an analytical system for a trace element, including a first flow passage and a second flow passage, wherein a sample is introduced in the first flow passage and then pre-treated in the first flow passage; the sample thus pre-treated is sampled from the first flow passage into the second flow passage; and components of the sample thus sampled are analyzed in the second flow passage. In such an analytical system, the first and second flow passages are substantially separated in pressure from each other.

In the analytical system of the present invention having the above configuration, since the second flow passage can be rendered substantially in a non-pressurized state even if the first flow passage is in a pressurized state, the pressurized portion of the entire flow passage is shortened so as to reduce a time required for measurement and hence to reduce dispersion of the sample, resulting in the reduced total cost of the system.

In the analytical system of the present invention having the above configuration, since the second flow passage is separated in pressure from the first flow passage, a sample which is sampled from the first flow passage into the second flow passage can be analyzed in a still state irrespective of the flow of the sample in the first flow passage, so that the sample is prevented from being rendered in a laminar flow, thereby enabling high accurate analysis of a low concentration sample.

BRIEF DESCRIPTION OF THE DRAWINGS

These and other objects, features and advantages of the present invention will become more apparent by reference to the following description, taken in connection with the accompanying drawings, in which:

FIG. 3 is a schematic view showing the states of a sample in a flow cell and detection patterns in the inventive analytical system and a prior art analytical system;

FIG. 4 is a diagram showing a modification of a flow cell portion shown in FIGS. 1 and 2; and FIG. 5 is a diagram showing a modification of a second sample introduction unit shown in FIGS. 1 and 2.

DETAILED DESCRIPTION OF THE PREFERRED EMBODIMENTS

Figure 1:
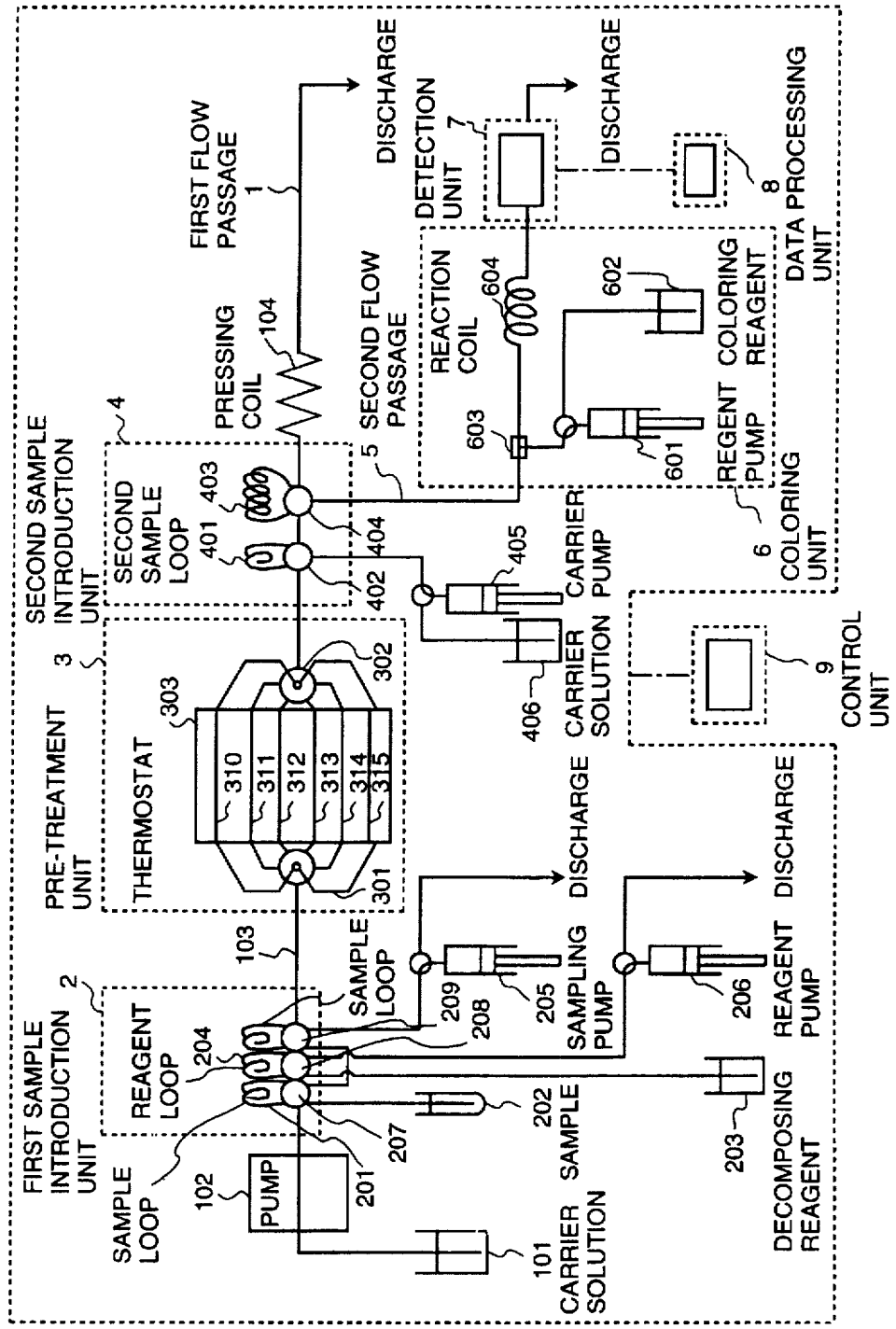
FIG. 1 is a diagram showing the entire configuration of an analytical system for a total nitrogen as one embodiment of analytical system for a trace element according to the present invention.

Prior to the detailed description of the preferred embodiments, the concept of the present invention will be described.

An analytical system for a trace element according to the present invention basically includes the following five components:

(1) a first flow passage pressurized for performing a pre-treatment, that is, decomposition by heating;

(2) a second sample introduction unit for sampling a sample decomposed by heating in the first flow passage and injecting the sample into the second flow passage;

(3) a second flow passage for performing a coloring operation;

(4) a detection unit for measuring the absorbance of a colored substance (reacted substance); and (5) a control unit for controlling these operations.

The first flow passage in (1) has a thermostat capable of being kept at 100° C. or more. A plurality of tubes are disposed in the thermostat, and multi-port valves are disposed in the upstream and downstream sides of the tubes for suitably selecting one of the tubes for one kind of sample. The first flow passage needs to be pressurized because the thermostat is heated up to a high temperature of 100° C. or more and thereby bubbles are liable to be produced in the tubes provided in the thermostat. After being injected-from a sample loop in the first sample introduction unit, a sample and a decomposing reagent are introduced in a suitable tube provided in the thermostat at a specified flow rate.

At this time, the multi-port valve is switched to introduce the next sample into another tube in the thermostat. In the general flow analysis, decomposition of the sample requires heating for a specified time, and the heating time is controlled by the length of the tube in the thermostat; however, in the embodiment of the present invention, the sample is decomposed by heating in a state being stayed for a suitable time in the tube by switching of the multi-port valves, and at the same time other samples can be similarly processed. This makes easy control of the heating/decomposition time and improvement in processing ability.

The tube provided in the thermostat may be made from platinum entirely or partially (only a portion in contact with solution), to improve a resistance against chemicals. It is to be noted that decomposition of a sample is not limited to be performed by heating, and may be performed by other methods, for example, by ultraviolet radiation. In this method using ultraviolet radiation, the material of the tube needs to be suitably changed.

In the sample introduction unit in (2), a second sample loop and a switching valve are provided in the downstream side of the thermostat. The switching valve is first switched in direction to the first flow passage side, and when the decomposed sample is introduced in the second sample loop, the switching valve is switched in direction to the second flow passage side. In this operation, the samples having a wide range from a low concentration to a high concentration can be analyzed or measured by provision of a plurality of sample loops in order that the decomposed sample can be made to selectively flow in a sample loop having a suitable length, and provision of a plurality of valves to the sample loops for sampling only part of the sample by switching timing of the valves and for sampling a suitable zone, such as a front, middle, or end zone of the sample by introduction timing of the sample into the second sample loop.

Where a total phosphorus and a total nitrogen are simultaneously or sequentially analyzed, the second sample introduction unit and the coloring unit are provided for each of analysis of a total phosphorus and analysis of a total nitrogen, wherein the sample decomposed using the same decomposing reagent is introduced both in a second sample loop for a total phosphorus and in a second sample loop for a total nitrogen. For measurement of a high concentration sample, the same mechanism as described above may be provided.

In the second flow passage in (3) for allowing the sample sampled by the second sample introduction unit to be mixed with a coloring reagent and hence to react therewith, a plurality of syringe pumps are used for injecting samples and coloring reagents into the second flow passage. The syringe pump, which is different from a plunger pump or peristaltic pump for continuously feeding a solution, is able to inject a specified amount of a carrier solution or a coloring reagent into a flow passage. Accordingly, when the sample is introduced into the second loop, the valve is switched in direction to the second flow passage side, so that the sample and the coloring reagent sampled by the syringe pumps are injected into the second flow passage and mixed to each other, to thus perform the coloring operation.

Since the syringe pump can be operated as required by controlling operation of the syringe pump, switching of the valve, and the like in term of time, the consumption of the coloring reagent is minimized, and also the control thereof is made easy.

The detection unit in (4) has a flow cell into which a substance (reacted substance) colored in the second flow passage is injected using the syringe pump, followed by measurement of absorbance at a specified wavelength. In the general flow analysis, the colored sample continuously flows in the flow passage and the flow cell, and the quantitative analysis is performed by reading of the peak value or a rear value on the basis of the flow pattern formed by the continuous flow. In such a method, however, a laminar flow is formed in the tube, and the concentration distribution of each sample in the tube becomes non-uniform. This has a difficulty in detection for a low concentration sample.

In the embodiment of the present invention, the use of the syringe pump allows the colored substance (reacted substance) fed in the flow cell to be stayed for a specified time in the flow cell for making uniform the concentration of the sample in the flow cell, and hence to realize the high accurate measurement (analysis) for a low concentration sample. In this case, the measurement range can be extended by disposing a plurality of flow cells having different optical lengths in the detection unit and by selecting a suitable optical length in accordance with the concentration range of the sample.

The use of a monochromatic light source such as a semiconductor laser or a light emitting diode as the light source of the detection unit is advantageous in reducing the total cost of the system.

The embodiment of the present invention will be concretely described. It will be noted that in the drawings, solid lines indicate pipes and dotted lines indicate basic function portions of the embodiment of the present invention, and that lengths of the pipes, measurement conditions and the like may be freely set unless otherwise specified in the following description.

FIG. 1 shows a typical analytical system for a total nitrogen according to the present invention.

A pressure pump 102, a first sample introduction unit 2, a pre-treatment unit 3, and a second sample introduction unit 4 are arranged in a flow passage 1. The flow passage 1, through which a carrier solution 101 continuously flows, is pressurized by a pressing coil 104.

The sample injection into the flow passage 1 through the first sample introduction unit 2 will be first described. A sample 202 (standard solution pertains to the concept of the sample) is introduced in a sample loop 201 by a sampling pump 205 and a decomposing reagent 203 is similarly introduced in a decomposing reagent loop 204 by a reagent pump 206, and they can be injected from the loops 201, 204 into the flow passage 1 by operation of switching valves 207, 208 and 209. Syringe pumps are used for the sampling pump and the reagent pump, which can be operated only when sample injection is required. The length of a tube 103 connecting the first sample introduction unit 1 to the pre-treatment unit 3 is so adjusted that the sample and the decomposing reagent thus injected is sufficiently mixed to each other until they reach the pre-treatment unit 3.

The pre-treatment unit 3 for performing heating/decomposition includes a thermostat 303 capable of being kept at 100° C. or more, multi-port valves 301, 302 provided at both the ends of the thermostat 303, and tubes 310 to 315 provided between the valves 301, 302. The temperature of the thermostat, the diameter of a hole of each valve, and the number of the tubes may be suitably set. The sample flowing in the tube 103 reaches the valve 301, and is introduced into a suitable tube, for example, the tube 310 by previously setting the direction of the valve 301. After the sample is introduced into the tube 310, the valve 301 is switched. Thus, the sample remains in the tube 310 disposed in the thermostat 303 and is decomposed by heating for a specified time. Meanwhile, another sample is similarly introduced into a suitable tube, for example, the tube 311 in the thermostat 303 by switching the valves 301 and 302, to be decomposed by heating. In this way, other samples are sequentially introduced into the tubes 312 to 315 until the decomposition of the sample in the tube 310 is completed, and thereafter, the samples will be subjected to subsequent treatments in the order from the sample in the tube 310 by switching the valves on the basis of time control, thus improving the processing ability.

In this case, the tubes 310 to 315 may be made from platinum to improve the decomposition efficiency. The platinum tube includes a tube having an inner surface coated with a platinum coating or a tube filled with platinized asbestos.

The decomposition is not limited to be performed by heating, and may be performed by ultraviolet radiation singly or in combination.

The second sample introduction unit 4 includes two sample loops 401, 403 having different lengths, and switching valves 402, 404. The sample having a high concentration is introduced into the short sample loop 401 and the sample having a low concentration is introduced into the long sample loop 403, and they are injected into the second flow passage 5 by operation of the valves 402, 404 respectively. The timing of the introduction of the sample thus decomposed into the sample loop 401 or 403 can be easily determined in accordance with the flow velocity of the sample in the first flow passage, the length of the tube from the pump 102 to the valve 402 or 404, the heating time for decomposition, and the like.

The second flow passage 5 includes a carrier pump 405 for injecting the sample sampled at the second sample introduction unit 4 into the second flow passage and a carrier solution 406, a reagent pump 601 and a reaction reagent 602 in the coloring unit 6, and a three-way joint 603 and a reaction coil 604. Syringe pumps are used for the pumps 405 and 601. After the sample is introduced into the second sample loop 401 or 403, the valve is switched in direction to the second flow passage side. At this time, the sample is injected into the second flow passage by the carrier pump 405 and the reaction reagent is injected at the coloring unit 6. The sample and the reaction reagent are mixed to each other in the reaction coil 604.

The use of the syringe pumps for feeding the sample and the reagent eliminates the need of usually feeding the carrier solution as in the first flow passage and keeps the second flow passage in a low pressure state, thereby reducing the cost required for construction of the second flow passage.

The detection unit 7, which includes a light source, a flow cell and a detector, is disposed in the downstream course of the coloring unit 6 of the second flow passage. The solution feeding amount of each of the pumps 405, 601 is adjusted by previously calculating the capacity from the second sample loop to the detection unit 7, so that the colored substance obtained by reaction of the sample and the coloring reagent each of which is fed by one vertical action of the syringe, is fed in the flow cell in the detector and is allowed to remain therein. After an elapse of a specified time required for stabilizing the absorbance since injection of the colored substance in the flow cell, the colored substance is measured in terms of the absorbance at a specified wavelength. The measured data are supplied to a data processing unit 8, whereupon they are processed.

A monochromatic light source such as a semiconductor laser or a light emitting diode may be used as a light source of the detection unit. The carrier solution 406 is fed by the pump 405 for cleaning the insides of the flow passage 5 and the flow cell of the detection unit 7, and thereafter the next sample is similarly measured.

The above operations are controlled by the control unit 8, to thus realize the present invention.

In the above embodiment, the colored sample is made to remain in the flow cell for a specified time until the absorbance thereof is stabilized as shown by reference numeral 750 in FIG. 3, so that the stabilized absorbance of the sample is measured. In this case, there may be adopted a method shown by reference numeral 760 in FIG. 3, in which the colored substance is allowed to pass through the flow cell just as the prior art flow injection analysis, and the concentration is calculated on the basis of the peak value or area value of the obtained flow pattern. However, in the method shown by reference numeral 760, the colored substance in the flow cell exhibits a laminar flow and thereby the concentration thereof is not uniform, and accordingly, the analysis of a low concentration sample should be performed using the method shown by reference numeral 750. In the general flow injection analysis, since both the carrier solution and the reagent usually flow in the flow cell, it is difficult to realize the method shown by reference numeral 750; however, in the embodiment of the present invention, the detection method shown by reference numeral 750 can be easily realized by the use of the syringe pumps.

The detection unit 7 may be so configured as shown in FIG. 4, in which flow cells 702, 703 having different optical lengths are disposed, wherein the solution feeding amount of each of the pumps 405 and 601 is adjusted such that the colored substance is injected into the flow cell 702 having the short optical length for the high concentration sample and it is injected into the flow cell 703 having the long optical length for the low concentration sample, thereby extending the measured range. In addition, reference numeral 701 indicates a light source, and 704 indicates a detector.

The second sample introduction unit may be so configured as shown in FIG. 5, in which a plurality of sample loops (for example, sample loops 480, 490) are provided in association with a plurality of switching valves in such a manner that part of the sample which is first sampled at the sample loop 480 is further sampled at the sample loop 490. Such an operation is particularly effective for measurement of a high concentration sample because the sample injected in the first sample introduction unit is further diluted at a high magnification.

On the other hand, analysis of a total phosphorus may be performed using a system similar to that used for analysis of a total nitrogen, in which the decomposing and reaction reagents for a total phosphorus are used and measurement conditions such as a heating time for decomposition and a measurement wavelength are suitably adjusted.

Figure 2:
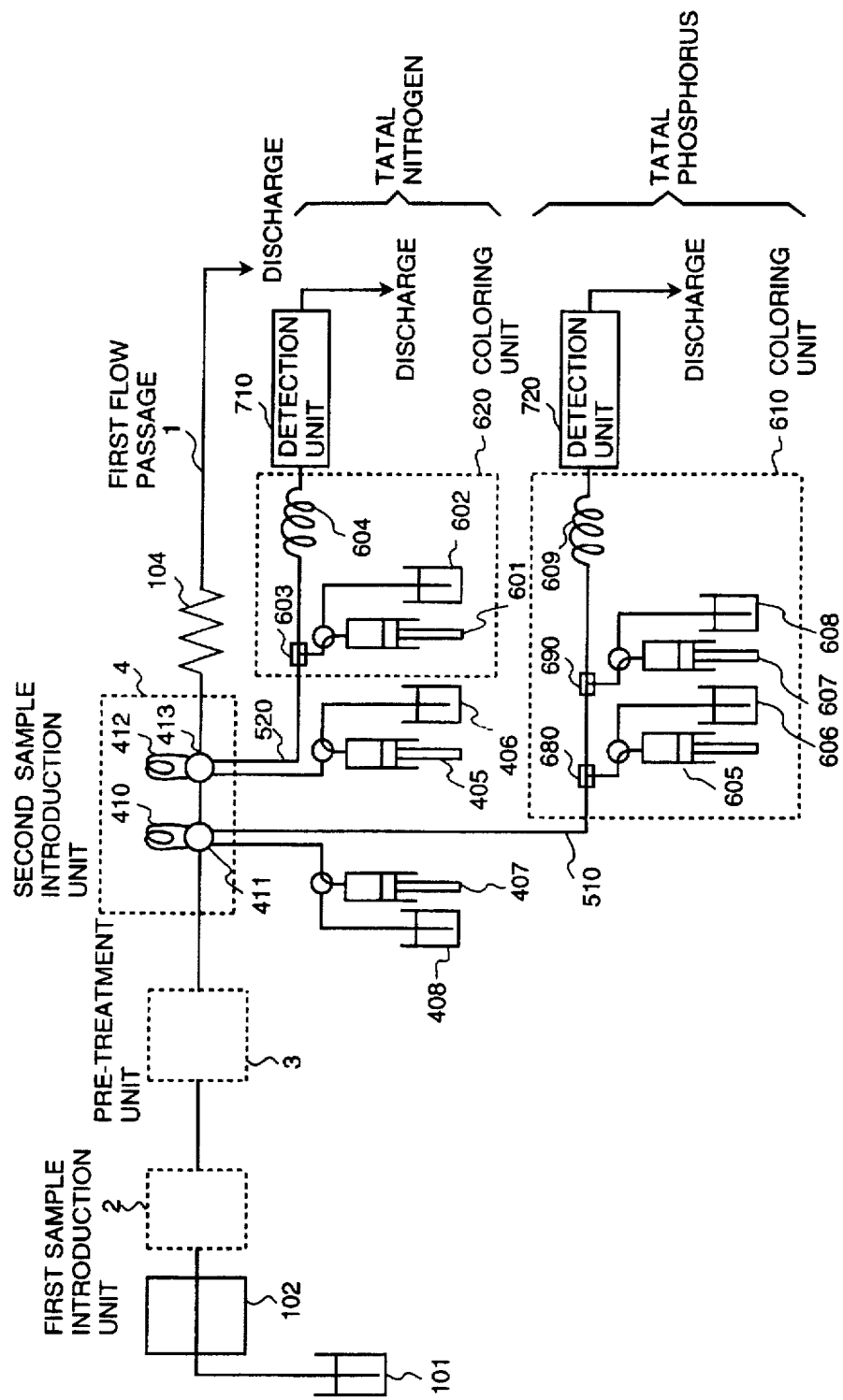
FIG. 2 is a diagram showing the entire configuration of an analytical system for a total phosphorus and a total nitrogen as another embodiment of the analytical system for a trace element according to the present invention.

FIG. 2 shows the configuration example of a system for simultaneously analyzing a total phosphorus and a total nitrogen using the same sample. This system is different from the system for analyzing a single component (total phosphorus or total nitrogen) as shown in FIG. 1 in that it includes a second flow passage 510 for analysis of a total phosphorus and a second flow passage 520 for analysis of a total nitrogen, and a detection unit 710 for detection of a total nitrogen and a detection unit 720 for detection of a total phosphorus.

The sample decomposed by heating in a first flow passage 1 is introduced into a sample loop 410 by carrier pump 407 for a total phosphorus and a sample loop 412 by carrier pump 405 for a total nitrogen in a second sample introduction unit 4, and then parts of the sample introduced in the sample loops 410, 412 are injected into the second flow passages 510, 520 by switching valves 411, 413, respectively. Associated with pumps 405 and 407 are respective carrier solution 406 and 408. For a high concentration sample, it may be diluted as shown in FIG. 5. In this case, the amount of the sample injected into the first flow passage 1 is in such a range as to sufficiently fill the sample loop 410 for a total phosphorus and the sample loop 412 for a total nitrogen in the second sample introduction unit 4.

For analysis for a total phosphorus, the sample injected in the second flow passage 510 is mixed with a coloring reagent 606 or 608, introduced respectively by a pump 605 or a pump 607, at a coloring unit 610, followed by coloring, and is measured in absorbance at a detection unit 720 for a total phosphorus. For analysis of a total nitrogen, the sample injected into the second flow passage 520 is mixed with a coloring reagent 602 for a total nitrogen, followed by coloring, and is measured in absorbance at the detecting unit 710 for a total nitrogen.

The second sample introduction unit 4, and the detecting units 710, 720 may be so configured as shown in FIGS. 4 and 5.

The system shown in FIG. 2 may be modified into a system for sequential analysis, in which it include one second flow passage in place of the second flow passages 510, 520 in FIG. 2 and also it is designed to inject into the second flow passage a suitable one of the reagents 606, 608 for a total phosphorus and the reagent 602 for a total nitrogen. In such a system, either of the samples sampled at the second sample loops 410, 412 is first analyzed in the manner shown in FIG. 1, and subsequently the other sample is similarly analyzed in the second flow passage.

As described above, the present invention provides an analytical system for a trace element, in which a pressurized portion of a flow passage is shortened so as to reduce a time required for stabilizing the flow and hence to reduce dispersion of a sample, resulting in the reduced total cost of the system. The present invention also provides an analysis system for a trace element, which enables high accurate analysis of a low concentration sample in a still and non-laminar flow state.

What is claimed is:

1. An analytical system for a trace element in a flow of fluid sample comprising:
   a first flow passage;
   a pump adapted to establish a pressurized flow in said first flow passage;
   a second flow passage;
   a sample introduction unit adapted to introduce a sample including said trace element into said first flow passage;
   a pre-treatment unit, provided in said first flow passage, adapted to pre-treat said introduced sample;
   a sampling unit adapted to sample said pre-treated sample from said first flow passage into said second flow passage in such a manner that the effect of pressurization in said first flow passage is isolated from said second flow passage so as to reduce dispersion of said sample with said trace elements therein;
   a reagent introduction unit adapted to introduce reagent into said second flow passage for reaction with said sample; and
   an analytical unit adapted to analyze components of said reacted sample sampled in said second flow passage.

2. An analytical system for a trace element according to claim 1, wherein said sampling unit includes a plurality of sample loops different in length or inside diameter for selectively sampling said pre-treated sample.

3. An analytical system for a trace element according to claim 1, wherein said sampling unit includes a first sample loop for sampling said pre-treated sample and a second sample loop for further sampling said sample thus sampled in said first sample loop, and the sampling timing from said first sample loop to said second sample loop is selectively performed.

4. An analytical system for a trace element according to claim 1, wherein said analytic unit is a spectrophotometric unit, and each of said sampling unit and a reagent introduction unit includes a pump.

5. An analytical system for a trace element according to claim 4, wherein each of said pumps is a syringe pump.

6. An analytical system for a trace element according to claim 5, wherein the measurement of said reacted substance in said analytical unit is performed in a state in which said reacted substance is still.

7. An analytical system for a trace element according to claim 4, wherein said analytical unit includes a plurality of flow cells having different optical lengths, and said unit allows said reacted substance to be selectively introduced into one of said flow cells for measurement of absorbance.

8. An analytical system for a trace element in a flow of fluid sample, comprising
   a first flow passage;
   a carrier introduction unit including a pump adapted to form a carrier solution flow pressurized in said first flow passage;
   a sample introduction unit adapted to introduce a sample into including said trace element said first flow passage;
   a reagent introduction unit adapted to introduce a decomposing reagent into said first flow passage so as to decompose said introduced sample;
   a second flow passage;
   a sampling unit adapted to sample said decomposed sample from said first flow passage into said second flow passage in such a manner that the effect of pressurization in said first flow passage is isolated from said second flow passage so as to reduce dispersion of said sample with said trace elements therein; and
   an analytical unit adapted to analyze components of said sample sampled in said second flow passage,
   said analytical unit including a unit adapted to introduce a coloring reagent into said second flow passage so as to allow said coloring reagent to react with said decomposed sample, and an instrument adapted to measure an absorbance of a reacted substance thus obtained.

9. An analytical system for a trace element in a flow of fluid sample, comprising:
   a first flow passage;
   a carrier introduction unit including a pump adapted to form a carrier solution flow pressurized in said first flow passage;
   a sample introduction unit adapted to introduce a sample with said trace element containing a total phosphorus and a total nitrogen as components to be measured into said first flow passage;
   a reagent introduction unit adapted to introduce a decomposing reagent into said first flow passage so as to decompose said introduced sample;
   a second flow passage including a flow passage for a total phosphorus and a flow passage for a total nitrogen;
   a sampling unit adapted to sample said decomposed sample from said first flow passage into said second flow passage in such a manner that the effect of pressurization in said first flow passage is isolated from said second flow passage; and an analytical unit adapted to analyze components of said sample sampled in said second flow passage, said analytical unit including a unit adapted to introduce a coloring reagent for a total phosphorus into said flow passage for a total phosphorus so as to allow said coloring reagent for a total phosphorus to coloredly react with said decomposed sample for obtaining a first reacted substance; a unit adapted to introduce a coloring reagent for a total nitrogen so as to allow said coloring reagent for a total nitrogen to coloredly react with said decomposed sample for obtaining a second reacted substance; an instrument adapted to measure an absorbance of said first reacted substance flowing in said flow passage for a total phosphorus; and an instrument adapted to measure an absorbance of said second reacted substance flowing in said flow passage for a total nitrogen.

10. An analytical system for a trace element according to claim 9, wherein the measurement of a total phosphorus and the measurement of a total nitrogen are substantially simultaneously or selectively performed.

11. An analytical system for a trace element in a flow of fluid sample, comprising:

a first flow passage;

a carrier introduction unit including a pump adapted to form a carrier solution flow pressurized in said first flow passage;

a sample introduction unit adapted to introduce a sample including said trace element containing a total phosphorus and a total nitrogen as components to be measured into said first flow passage;

a reagent unit adapted to introduce a decomposing reagent into said first flow passage so as to decompose said introduced sample;

a second flow passage;

a sampling unit adapted to sample said decompose sample from said first flow passage into said second flow passage in such a manner that the effect of pressurization in said first flow passage is isolated from said second flow passage said sampling unit adapted to sample said decomposed sample into said second flow passage twice with a time difference to prepare a sample for a total phosphorus and a sample for a total nitrogen; and an analytical unit adapted to analyze components of said sample sampled in said second flow passage, said analytical unit including a unit adapted to introduce a coloring reagent into said second flow passage so as to allow said coloring reagent to react with said decomposed sample, and an instrument measuring an absorbance of a reacted substance thus obtained and adapted to sequentially analyze said total phosphorus and said total nitrogen contained in said respective samples sampled in said second flow passage.

12. An analytical system for a trace element in a flow of fluid sample, comprising:

a first flow passage;

a carrier introduction unit including a pump adapted to form a carrier solution flow pressurized in said first flow passage;

a sample introduction unit adapted to introduce a sample including said trace element into said first flow passage;

a reagent introduction unit adapted to introduce a decomposing reagent into said first flow passage so as to decompose said introduced sample configured as to sequentially take samples in said first flow passages;

a thermostat adapted to perform decomposition at a temperature of 100° C. or more, said thermostat containing a plurality of tubes capable of being selectively connected to said first flow passage by switching of valves, a heating/decomposition time required for each of a plurality of samples being controlled by introducing a sample injected in said first flow passage into an arbitrary one of said tubes and subsequently introducing another sample into another tube by switching of a valve, thereby allowing said sample introduced in said arbitrary tube to remain therein for a specified time and heating/decomposing it using said decomposing reagent, and then returning said decomposed sample again into said first flow passage, and repeatedly performing this operation for a plurality of samples;

a second flow passage;

a sampling unit adapted to sample said decomposed sample from said first flow passage into said second flow passage in such a manner that the effect of pressurization in said first flow passage is isolated from said second flow passage; and an analytical unit adapted to analyze components of said sample sampled in said second flow passage, said analytical unit including a unit adapted to introduce a coloring reagent into said second flow passage so as to allow said coloring reagent to react with said decomposed sample, and an instrument adapted to measure an absorbance of a reacted substance thus obtained.

13. An analytical system for a trace element according to claim 12, wherein said tube disposed in said thermostat has a solution contact portion made from platinum.

14. An analytical system for a trace element in a flow of fluid sample, comprising:

a first flow passage;

a carrier introduction unit including a pump adapted to form a carrier solution flow pressurized in said first flow passage;

a sample introduction unit adapted to introduce a sample including said trace element into said first flow passage;

a reagent introduction unit adapted to introduce a decomposing reagent into said first flow passage so as to decompose said introduced sample;

a second flow passage;

a sampling unit adapted to sample said decomposed sample from said first flow passage into said second flow passage in such a manner that the effect of pressurization in said first flow passage is isolated from said second flow passage including a sample loop adapted to measure a total phosphorus and a sample loop adapted to measure a total nitrogen, whereby parts of said decomposed sample, which are introduced into said sample loops, are selectively introduced by switching of valves; and an analytical unit adapted to analyze components of said sample sampled in said second flow passage, said analytical unit including a unit adapted to introduce a coloring reagent into said second flow passage so as to allow said coloring reagent to react with said decomposed sample, and an instrument adapted to measure an absorbance of a reacted substance thus obtained.

15. An analytical system for a trace element according to claim 7, wherein said absorbance measuring means includes a monochromatic light source.

* * * * *